United States Patent [19]
Britto et al.

[11] Patent Number: 6,098,619
[45] Date of Patent: Aug. 8, 2000

[54] UNIT DOSE INHALER APPARATUS AND METHOD OF DELIVERY USING SAME

[75] Inventors: Ignatius Loy Britto, Cary, N.C.; Jason Christopher Billig, Chicago, Ill.; Fredric Scott Stiber, Houston, Tex.

[73] Assignee: Glaxo Wellcome Inc., Research Triangle Park, N.C.

[21] Appl. No.: 09/302,202

[22] Filed: Apr. 29, 1999

Related U.S. Application Data

[60] Provisional application No. 60/084,038, May 4, 1998.

[30] Foreign Application Priority Data

May 13, 1998 [DE] Germany ................ 9810126

[51] Int. Cl.[7] .................. A61M 15/00; A61M 16/00; B05D 7/14; B05D 83/06
[52] U.S. Cl. ................ 128/203.15; 128/203.12; 128/203.21; 128/203.28
[58] Field of Search .............. 128/200.12, 200.14, 128/200.22, 202.18, 203.12–203.15, 203.21–203.28, 204.13, 205.13, 205.21; 204/438; 222/106, 630

[56] References Cited

U.S. PATENT DOCUMENTS

| | | | |
|---|---|---|---|
| 1,985,001 | 12/1934 | Thometz | 128/203.12 |
| 2,318,636 | 5/1943 | Schaaff | 128/203.12 |
| 2,598,823 | 6/1952 | O'Grady | 128/203.12 |
| 3,788,316 | 1/1974 | Mora | 128/203.12 |
| 3,949,751 | 4/1976 | Birch et al. | |
| 4,508,116 | 4/1985 | Duncan et al. | |
| 5,038,431 | 8/1991 | Burgin et al. | 5/438 |
| 5,582,162 | 12/1996 | Petersson | |

FOREIGN PATENT DOCUMENTS

| | | | |
|---|---|---|---|
| 93/09831 | 5/1993 | WIPO | 128/203.12 |

Primary Examiner—John G. Weiss
Assistant Examiner—Joseph F. Weiss, Jr.
Attorney, Agent, or Firm—James P. Riek

[57] ABSTRACT

An inhaler apparatus having a housing having first and second walls and defining an air inlet and an air outlet. The first and second walls define an internal housing volume and have portions being movable relative to each other so as to expand the internal housing volume from a non-inhalation state, wherein the internal housing volume has a first volume, to an inhalation state, wherein the internal housing volume has a second volume. The second volume is larger than the first volume. An air flow chamber is defined within the housing between the air inlet and the air outlet when the housing is in the inhalation state. A medicament is contained between the first and second walls. The medicament is exposed within the air flow chamber when the housing is in the inhalation state.

34 Claims, 8 Drawing Sheets

UNIT DOSE INHALER APPARATUS AND METHOD OF DELIVERY USING SAME

CROSS-REFERENCE TO RELATED APPLICATIONS

This application claims benefit of priority under 35 USC 119(e) from provisional application Ser. No. 60/084038 filed May 4, 1998.

TECHNICAL FIELD

The present invention relates generally to inhaler apparatuses, and more particularly, to compact, environmentally friendly, inexpensive dry powder unit dose inhalers.

BACKGROUND ART

As appreciated by those of skill in the art, it is often beneficial to administer therapeutic or diagnostic agents (herein referred to variously as "medicaments", "medications", or "drugs") to the lungs or through the lungs of a patient. For certain medical conditions, topical administration of medication to the lung is often the preferred way to provide relief to the patient. For example, in the case of an acute asthma attack, direct "rescue" administration of medications such as albuterol directly to the smooth muscle of a patient's lungs provides for immediate relief of bronchial inflammation.

Systemic delivery or administration of medicament by inhalation to the blood stream via the alveolar blood vessels, may also provide advantages over standard oral or intravenous systemic delivery regimes. For example, in comparison with oral dosing, systemic delivery via the lung can increase bioavailability of some medications by avoiding metabolic inactivation of the medicament in the gut or liver. Respiratory delivery to the blood stream also avoids the potential risk of disease transmission from using intravenous delivery devices such as hypodermic needles.

Many devices exist in the art which are useful for delivering medicaments via the inhaled route, including propellant based metered dose inhalers (MDIs). Due to environmental concerns over ozone depletion, MDIs using chlorofluorocarbons as propellants are being phased out in favor of more environmentally friendly powder inhalers.

Dry powder inhalers, which lack any propellants whatsoever, are viewed as one solution to the alleged problem caused by ozone depleting propellants. Dry powder inhalers are of three basic varieties: Reservoir based Dry Powder Inhalers (RDPIs); Multi-unit dose Dry Powder Inhalers (MDPIs); and Unit dose Dry Powder Inhalers (UDPIs). RDPIs meter doses in the device out of a powder reservoir to provide multiple doses of medication, while MDPIs contain multiple premeasured, individually packaged doses of drugs. UDPIs, in comparison, contain a single dose of medicament.

Despite the desirability of drug delivery via inhalation and the preferability of dry powder inhalers, it is often difficult to obtain a patient's full compliance with prescribed instructions for an inhaled medicament, and reasons for non-compliance may vary. Patients may fail to fully comply with prescribed dosing because of awkwardness of the size or shape of their inhaler. The dry powder inhalers currently known in the art, for the most part, tend to be bulky and, therefore, awkward to carry on one's person. The awkwardness of carrying such devices contributes to a patient's failure to have the inhaler available during daily activities. For some individuals in need of "rescue" applications of medication, such as patients with severe asthma or athletes experiencing exercise-induced asthma attacks, this can be a significant disadvantage to inhaler design. Bulky, cumbersome inhalers are ill-suited for such purposes.

Another reason patients might not comply with prescribed dosing is that they may perceive a social stigma from using their inhalers in public. In some cases, patients may feel embarrassed or self-conscious about using a cumbersome inhaler in public places and therefore, may not carry and/or use the inhaler as prescribed by their doctors.

A still further reason for patients not using inhalers may include the patient's inability to afford the devices at all due to limited financial resources. Complexity of a device adds to its cost, and the more expensive a device is, the less accessible it may be to all potential users.

UDPIs are generally speaking less complex, more compact and less expensive than RDPIs and MDPIs. Moreover, RDPIs and MDPIs are not ideally suited for delivering therapies only needing a single application, especially where disposability after use is a desirable feature. Prior art UDPIs, unfortunately, in some instances remain relatively bulky and awkward and may be made from environmentally unfriendly, non-biodegradable materials, such as certain plastics.

Examples of prior art UDPIs include that disclosed in U.S. Pat. No. 5,645,051 to Schultz, which describes a plastic and metal unit dose dry powder inhaler having a motor driven impeller. PCT Patent Publication No. WO 97/05918 to Asking discloses a UDPI having a dry powder dose sandwiched between two peelable cover strips. The cover strips are pulled from the device, thus internally exposing the drug in a flow path. PCT Publication No. 96/222802 assigned to Directhaler discloses a straw-like UDPI having a dose contained within the straw and which is sealed by removable end caps.

Despite the existence of various prior art unit dose dry powder inhalers, there remains much room for improvement in the art. Specifically, there exists a long-felt need for a UDPI apparatus and method of use wherein the inhaler apparatus is inexpensive, disposable, environmentally friendly, simple, compact and easily carried and used by a patient, so as to increase patient compliance, and yield improved drug delivery.

DISCLOSURE OF THE INVENTION

In accordance with the present invention, a unit dose inhaler apparatus and method of use are described. The inhaler apparatus comprises a flexible housing having first and second walls. The housing defines an air inlet and an air outlet and an internal housing volume. The housing is preferably deformable or expandable so as to expand the housing volume from a non-inhalation state having a first housing volume, to an inhalation state having a second housing volume. The second housing volume is greater than the first housing volume. An air flow chamber is defined within the housing between the air inlet and the air outlet when the housing is in its inhalation state.

A medicament dose, which may be a therapeutic or diagnostic agent, is positioned within the housing between the first and second walls. The medicament is sealed from the outside environment in the non-inhalation state. This sealed arrangement prohibits the medicament from falling out of the device, and also prevents air and moisture ingress into the device, thus preserving the sterility and stability of the medicament dose.

In use, the housing volume is expanded to its inhalation state, increasing the distance between at least portions of the interior surfaces of the first and second walls. The movement of the walls exposes the medicament contained in the housing within the air flow chamber. A patient inhales through the air outlet and entrains the medicament in an inhalation stream. The medicament flows through the inhalation stream, where it may pass directly to the air outlet and into the patient's lungs. Alternatively, the dosage may first be deagglomerated before passing to the air outlet and into the patient's lungs, for instance, by impacting on various surfaces in the device, or through vibrational effects provided by components within the device.

The UDPI of the present application may further include one or more one-way valves to allow airflow from the device to the patient's lungs, but prevent the user from exhaling through the device, so as to blow the drug out of the device.

A wide variety of mechanisms may be used to seal the medicament within the device, to deagglomerate the powdered drug upon inhalation, or to act as a valve, as is described in more detail below.

Accordingly, it is an object of this invention to provide a novel UDPI apparatus and method of using the same.

It is another object of this invention to provide a UDPI apparatus that is small, compact and easily carried.

It is a further object of this invention to provide a UDPI apparatus that is expandable and has a larger internal volume when it is in an inhalation state than it has when it is in a non-inhalation state.

It is a still further object of this invention to provide a UDPI apparatus that is inexpensive to manufacture.

It is a still further object of this invention to provide a unit dose inhaler device which may be disposed of with minimal environmental impact.

It is a still further object of the present invention to provide a UDPI where the medicament contained therein is preserved in a sealed fashion until ready to use.

It is a still further objection of the present invention to provide a UDPI with a deagglomeration mechanism to break up dry powder agglomerates to provide a greater percentage of powder particles within the respirable range.

It is a still further object of the present invention to provide a UDPI apparatus which a user may inhale through but may not exhale through so as to prevent loss of medicament prior to it being delivered to the lung.

Lastly, it is an object of the present invention to provide a UDPI apparatus and method of use that facilitates patient compliance with prescribed instructions for the medicament within the inhaler by being easy to use.

Some of the objects of the invention having been stated hereinabove, other objects will become evident as the description proceeds, when taken in connection with the accompanying drawings as best described hereinbelow.

DETAILED DESCRIPTION OF THE INVENTION

In accordance with the present invention, a UDPI apparatus and method of use are disclosed wherein the UDPI can be activated by inhalation by the user. No propellent, other than the force of the user inhaling the medicament, is required to operate the present unit dose inhaler apparatus. Preferably, the unit dose inhaler apparatus comprises a paper material, such as a 14–16 point solid bleached sulfate (SBS) laminated with 00035 foil or TYVEK®, manufactured by DuPont, that is capable of being dye cut according to the structures described hereinbelow. Thus, the unit dose inhaler apparatus of the instant invention can be discarded after the unit dose is taken by the patient. It is envisioned, however, in accordance with this invention that any other suitable material or materials could be used for construction of the present unit dose inhaler apparatus.

Referring now to the drawings, wherein like reference symbols refer to like parts throughout, the unit dose inhaler apparatus of the present invention is referred to generally as 10. Referring particularly to FIGS. 1 through 4, inhaler apparatus 10 comprises a flexible housing, generally referred to as 12. Housing 12 includes an integral first wall 14 and an integral second wall 16 and possesses an internal housing volume 13 (not shown in FIGS. 1–4). As will be described hereinbelow with respect to additional or alternative embodiments, the walls of other embodiments of the inhaler apparatus of this invention can be separate but abutting with various configurations of the housing.

Figure 1:
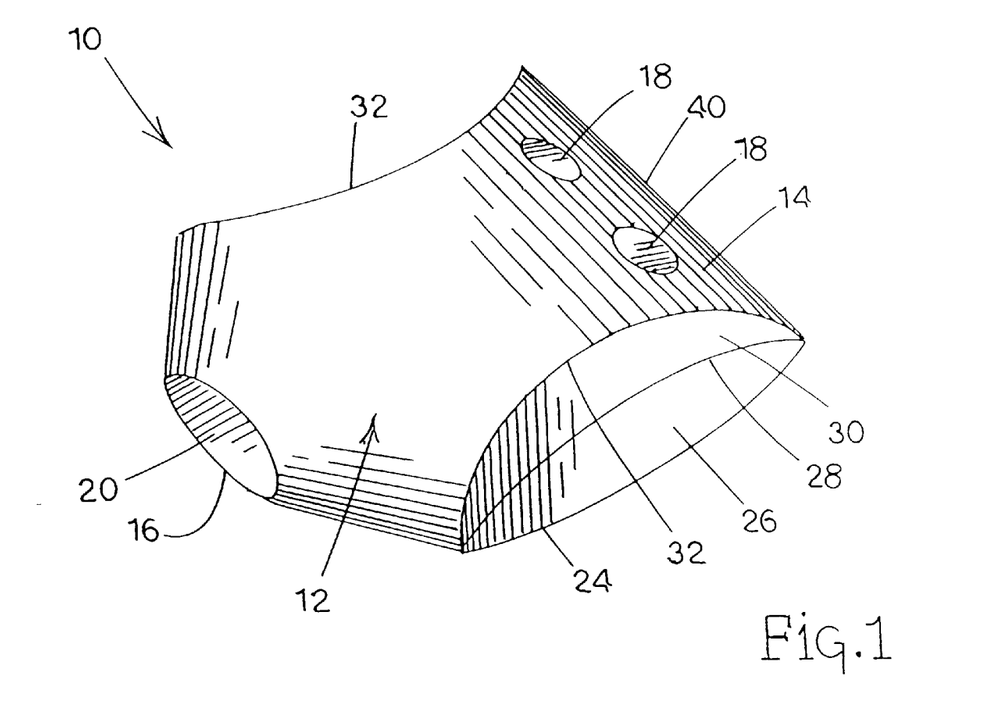
FIG. 1 of the drawings is a perspective view of an assembled inhaler apparatus of the present invention in an inhalation state.
Figure 2:
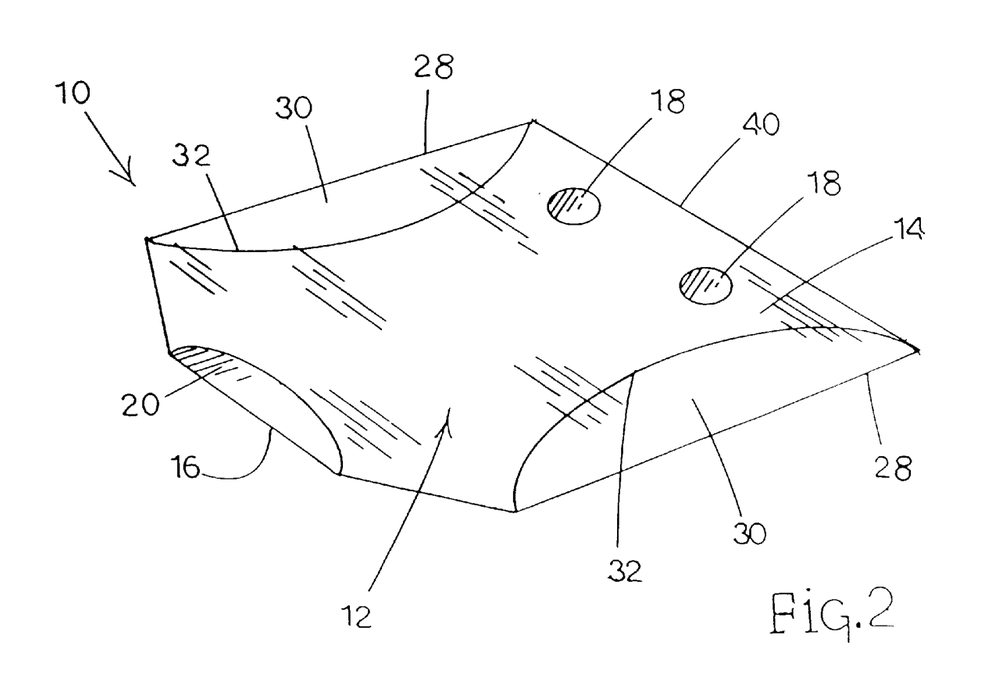
FIG. 2 of the drawings is a perspective view of an assembled inhaler apparatus of the present invention in a non-inhalation state.

As best seen in FIG. 1, housing 12 further comprises an air inlet port 18, which, preferably takes the form of a pair of spaced-apart but proximate air inlet ports on first wall 14 of housing 12. Housing 12 also comprises a mouthpiece or air outlet port 20 defined by portions of both first wall 14 and second wall 16 and substantially on the opposite side of housing 12 from air inlet port 18.

Figure 3:
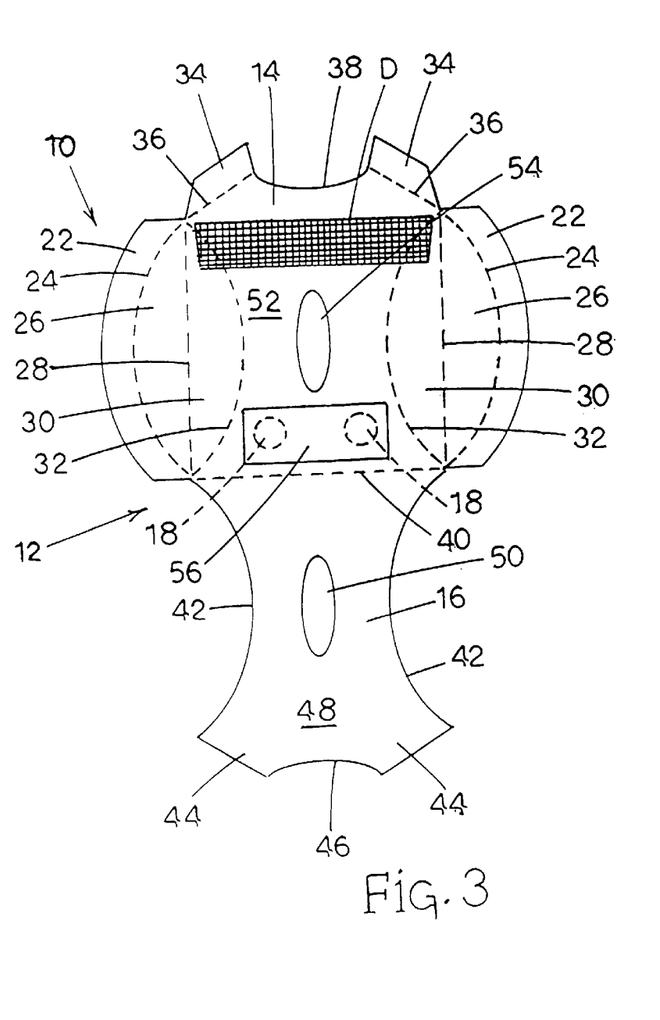
FIG. 3 of the drawings is an interior plan view of an unassembled inhaler apparatus of the present invention.
Figure 4:
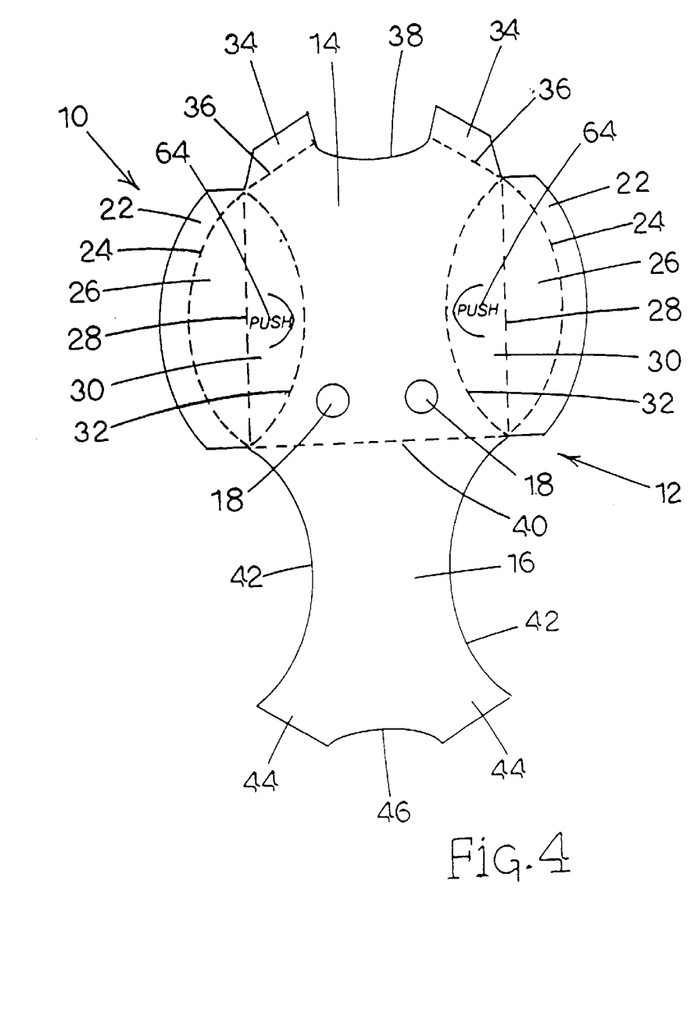
FIG. 4 of the drawings is an exterior plan view of an unassembled inhaler apparatus of the present invention.

As best seen in FIGS. 3 and 4, first wall 14 of housing 12 further comprises a series of flaps and folds by which first wall 14 is connected to second wall 16 and by which expandability is imparted to the internal housing volume 13 of housing 12. First wall 14 comprises a pair of outer side flaps 22 extending laterally therefrom with side flaps 22 being foldably attached along lower folds 24 to side walls 26, which are formed between lower folds 24 and medial side wall folds 28. Upper side walls 30 are formed between medial side wall folds 28 and upper folds 32.

Distal tabs 34 are formed along a distal edge of first wall 14 and are foldable along fold 36. Between distal tabs 34 is formed an arcuate segment 38. Primary fold 40 is defined along proximal edges of walls 14 and 16 and forms a connection between walls 14 and 16 of housing 12. Lateral arcuate edges 42 extend away from primary fold 40 in an arcuate path along the periphery of second wall 16. Projections 44 are defined between arcuate lateral edges 42 of second wall 16 and arcuate segment 46. Thus, arcuate segment 46 is defined along the distal edge of second wall 16 of housing 12 and lies between projections 44. As best seen in FIG. 4, instructional indicia 64 can be placed on first wall 14.

Second wall 16 of housing 12 has an interior surface 48. First wall 14 of housing 12 defines an interior surface 52. As shown in FIG. 3, valve flap or filter flap 56 is attached on interior surface 52 of first wall 14, such that filter flap 56 covers air inlet port 18.

Figure 3A:
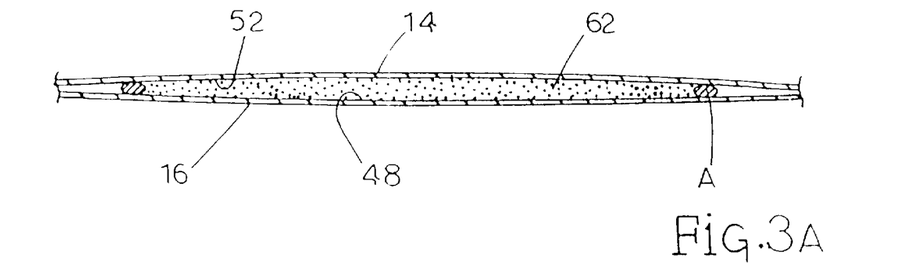
FIGS. 3A, 3B and 3C of the drawings are enlarged, isolated cross-sectional views of alternative structures for confining medicament in an inhaler apparatus of the present invention.
Figure 3B:
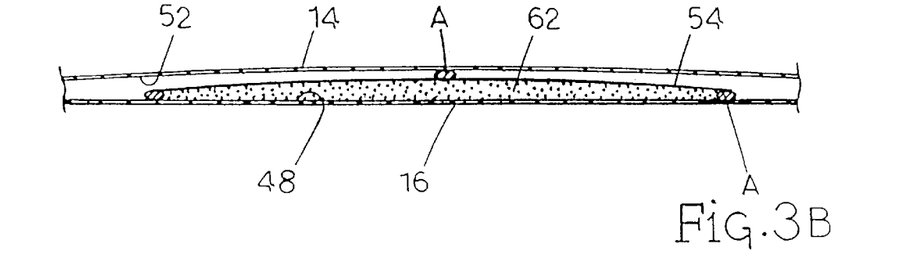
Figure 3C:
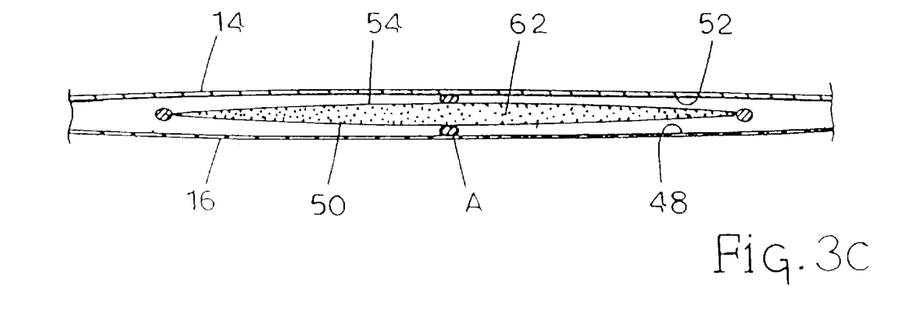

Continuing with particular reference to FIG. 3, second wall 16 of housing 12 further comprises interior surface 48. First wall 14 of housing 12 further comprises interior surface 52. Interior surfaces 48 and 52 are designed to contain, in various ways, a medicament dose 62. In one embodiment of the present invention and as shown in FIG. 3A, medicament dose 62 can be positioned between interior surfaces 48 and 52 without the use of a separate cover layer (the significance of which is described below with reference to the second and third embodiments) when, during assembly, first wall 14 is folded over second wall 16 (along primary fold 40), such that internal surfaces 48 and 52 face each other. Interior surfaces, 52 and 48, respectively, can, by virtue of an adhesive A encircling dose 62, form a dose or medicament holder 58 (FIG. 5), which defines an internal holder volume 60 for containing dose 62. In a second embodiment and as shown in FIG. 3B, medicament holder 58 is formed by a single holder cover portion 54 which is adhesively bonded by adhesive A to interior surface 48, with dose 62 sandwiched therebetween. In a third embodiment and as shown in FIG. 3C, medicament holder 58 is formed between a first holder cover portion 50 and a second holder cover portion 54 which are bonded together by adhesive A with dose 62 sandwiched therebetween.

The first of the three embodiments described above may be assembled by first metering a quantity of a medicament into interior surface 52 of first wall 14. A pressure-sensitive and biologically safe adhesive A is then spread around medicament 62. The adhesive is preferably a natural rubber base, pressure-sensitive adhesive preferably having the property of not sticking to anything but its own substrate and to itself after it dries. Booth, K. N. ed. *Industrial Packing Adhesives*, Blackey: Glasgow, 1990. Outer side flaps 22 of first wall 14 are then folded along medial side wall folds 28, and tabs 34 are folded along folds 36. The preferred natural rubber adhesive is then placed along the surfaces of side flaps 22 and tabs 34 that face second wall 16. Second wall 16 is then folded along primary fold 40 and moved into contact with side flaps 22 and tabs 34. Second wall 16 is moved in such a manner so as to ensure that arcuate segments 38 and 46 are adequately aligned to form air inlet port 20. Suitable pressure is then applied to second wall 16 so that the pressure-sensitive adhesive A on the abutting surfaces of side edges 22, tabs 34, and around medicament 62 adequately adheres between first and second walls 14, 16. So arranged, adhesive A surrounding medicament 62 confines the medicament 62 to the space between the interior surfaces 52 and 48 of the first and second walls 14 and 16 to form medicament holder 58.

Figure 5:
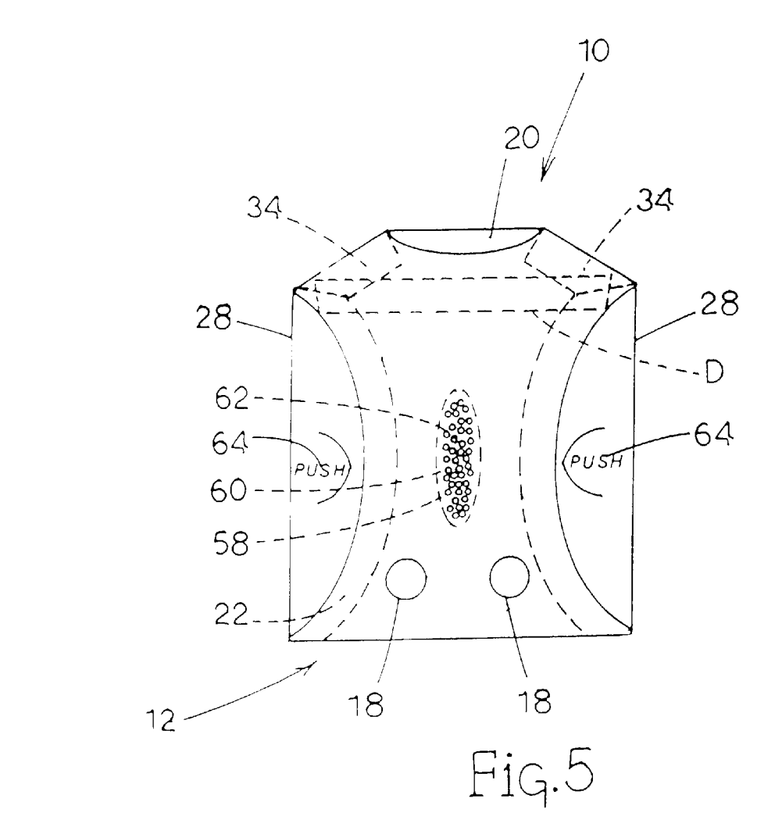
FIG. 5 of the drawings is a top plan view of an assembled inhaler apparatus of the present invention in a non-inhalation state.

In the second embodiment (FIG. 3B) of the present invention mentioned above, single medicament cover portion 50 can be used within inhaler 10. Cover portion 50 may be made of any suitable material, a metal or plastic foil being most preferred. In this second embodiment, and as seen in FIGS. 3–5, the single medicament holder cover portion 50 can be mounted with adhesive A on interior surface 52 generally in a medial position. As would be understood, mounting could also be made on the interior surface 48 of second wall 16 without departing from the scope of the present invention. Medicament dose 62 is then loaded onto cover portion 50 and a suitable adhesive is then spread around medicament 62 about the periphery of cover portion 54. The device is assembled as described above in the discussion of the first embodiment, thus forming an adhesive bond between interior surface 48 of second wall 16 and the peripheral edge of cover portion 50. So constructed, medicament holder 58 is formed between cover portion 50 and interior surface 48.

In the third embodiment (FIG. 3C) described above, medicament holder 58 is formed from a pair of cover portions 50 and 54 which when sealed together to form an envelope for containing medicament 62. The envelope for medicament holder 58 may be formed by positioning first holder cover portion 50 on interior surface 52 of first wall 14, and second holder cover portion 54 on interior surface 48 of second wall 16. A suitable adhesive is then applied to the periphery of one of the cover portions, and the inhaler is assembled, as described above. When assembled, medicament cover portions 50 and 54 of second and first walls 16 and 14, respectively, overlap for sealing medicament 62 within an internal volume 60 within medicament holder 58.

In this third embodiment, medicament holder 58 may also be made as a discrete unit, separately from the rest of the inhaler apparatus. In this alternative, medicament holder 58 is fabricated by metering the selected medicament onto a first cover portion. A second cover portion is placed over the deposited medicament and the cover portions are sealed together using heat, adhesive or any other suitable means known to those skilled in the art to form holder 58. The assembled medicament holder 58 may then be adhered with inhaler 10 on either interior surface 52 or 48, and assembly completed as described herein.

In a still further embodiment (not shown), medicament holder 58 can be defined by the internal volume of housing 12. In this embodiment, cover slips are used to seal air inlet port and air outlet port 18 and 20, respectively, thus sealing medicament 62 within housing 12.

Techniques for metering particulate medicaments are well known to those of ordinary skill. Suitable techniques include measuring volumes or weights of medicament directly onto surface 48, or cover portion 54, such as by vacuum tube; evaporation from suspension or solution, or by electrostatic deposition. In addition to metering particulate medicaments into medicament holder 58, medicaments may also be placed on or into a suitable carrier such as beads, meshes, fibrous materials of films, as discussed for example in U.S. Pat. Nos. 5,619,984 and 5,647,347, both of which are hereby incorporated by reference. These alternate substrates may be positioned in the internal housing volume as would be recognized by those of ordinary skill, to achieve substantially the same function and result in substantially the same was described above.

Medicament 62 may comprise any diagnostic or therapeutic agent that is suitable for inhalation. Generally, particles suitable for respiration have an aerodynamic diameter of between 0.5 and 10 micrometers. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketoifen or nedocromil; antiinfectives, e.g., cephalosporins, penicillins, streptomycin, sulphonamides, tetracyclines and pentamidine; antihistamines, e.g., methapyrilene; antiinflammatories, e.g., heclomethasone dipropionate, fluticasone propionate, flunisolilde, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (—)-4-amino-3,5-dichloro--[[[6-2-(2-pyridinyl)ethoxy)]hexyl] methyl] benzenemethanol; diuretics, e.g., amiloride; anticholinergics, e.g., ipratropium, tiotroprium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines; diagnostics; and gene therapy agents. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

Combinations of medicaments may be premixed compounds delivered in a single medicament holder. Alternatively, combinations may be single compounds individually packaged in separated medicament holders, with combinations of such different medicaments being presented in the same device.

Indeed, it is envisioned in accordance with this invention that any suitable therapeutic or diagnostic agent can be included as medicament 62 within medicament holder 58 or the present UDPI apparatus. The medicament may be a pure drug, or drug mixed with an excipient, for example, lactose.

OPERATION AND USE OF THE UNIT DOSE INHALER APPARATUS

Figure 6:
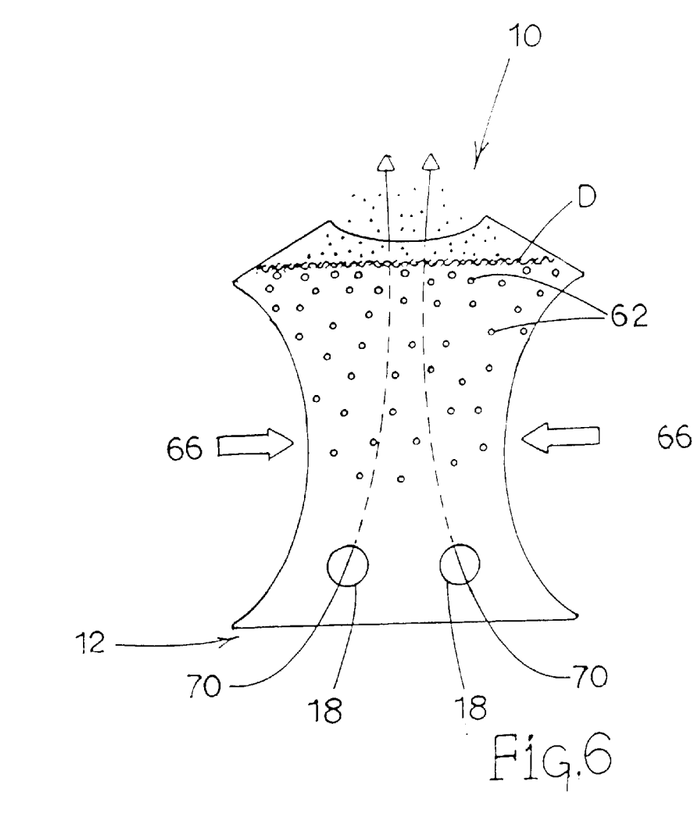
FIG. 6 of the drawings is a top plan view of the inhaler apparatus of the present invention in an inhalation state.

Referring now to FIGS. 5 through 8, the preferred method of operation and use of inhaler apparatus 10 is described. In FIG. 5, a ready-to-use inhaler apparatus 10 is presented wherein the internal housing volume 13 of housing 12 can be minimal, even zero, in a non-inhalation state. Medicament holder 58 having an internal volume 60, and including medicament 62 within its internal volume 60, is presented in phantom as it is contained within the interior of apparatus 10. Apparatus 10 can further comprise instructional indicia 64 which advise the user as to the direction in which the user must push medial side wall folds 28 to place inhaler apparatus 10 in its operable position. In use then, as best seen in FIG. 6, the user pushes inwardly along the direction of arrows 66, and after placing air outlet port 20 next to his or her mouth, then inhales through air outlet portion 20. Applying pressure in the direction of arrow 66 deforms and expands housing 12 and internal housing volume 13 from the non-inhalation state of FIG. 5 to the inhalation state of FIGS. 6 through 8. An air flow chamber 68 is simultaneously formed within housing 12 between air inlet ports 18 and air outlet port 20. Air flow can be created between air inlet ports 18 and air outlet port 20 by inhalation by the user as illustrated by air flow arrows 70. Expansion of housing 12 to an inhalation state preferably pulls medicament holder cover portion 54, which is mounted on the interior surface 52 of first wall 14, away from medicament holder portion 50, which is mounted on the interior surface 48 of second wall 16. Thus, the expansion of housing 12 to the inhalation state pushes walls 14 and 16 away from each other to break the seal between medicament holder portion 50 and medicament holder cover portion 54, thereby opening medicament holder 58. Medicament 62 contained within internal holder volume 60 of medicament holder 58 is thus exposed to air flow chamber 68 and the air flow along arrows 70 once the user inhales through air outlet port 20 to create the air flow represented by arrows 70. Medicament 62 then flows along air flow depicted by arrows 70 into the mouth and ultimately into the lungs of the user, where medicament 62 is delivered to the desired location within the lung. Preferably, then, medicament 62 is exposed to air flow within air chamber 68 simultaneously with the expansion of housing volume 13 of housing 12.

Figure 7:
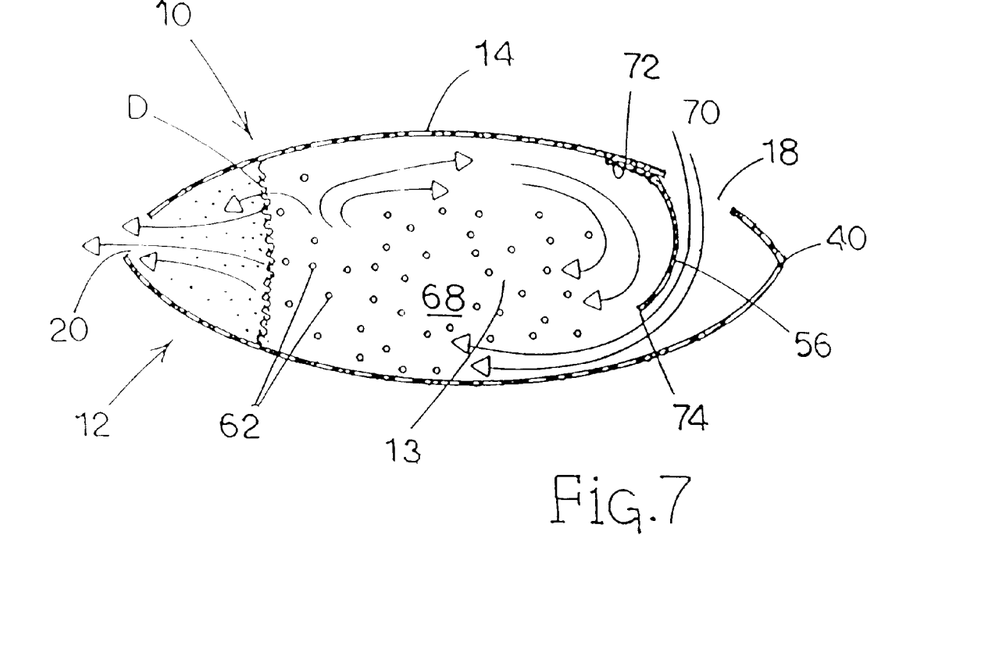
FIG. 7 of the drawings is a cross-sectional side view of the inhaler apparatus of the present invention in an inhalation state wherein filter flap 56 is shown in one manner of attachment.
Figure 8:
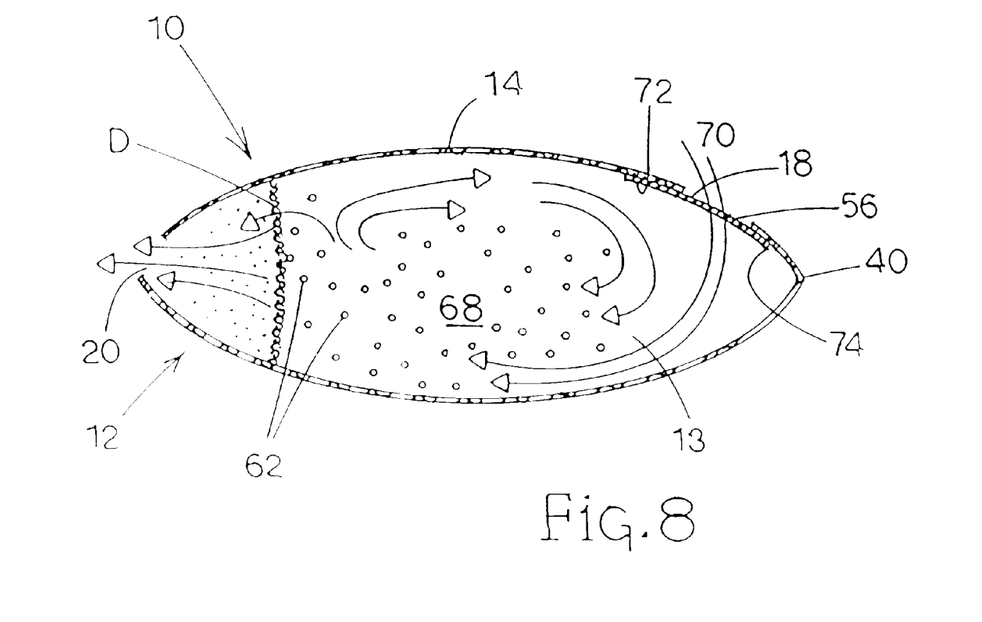
FIG. 8 of the drawings is a cross-sectional side view of the inhaler apparatus of the present invention in an inhalation state wherein filter flap 56 is shown in an alternative manner of attachment.

In use then, as best seen in FIG. 6, the user pushes inwardly along the direction of arrows 66 to laterally compress housing 12 to deform and expand housing 12 and internal housing volume 13 from the non-inhalation state of FIG. 5 to the inhalation state of FIGS. 6 through 8. An air flow chamber 68 is simultaneously formed within housing 12 between air inlet ports 18 and air outlet port 20. Air flow can be created through air inlet ports 18 and air outlet port 20 by inhalation by the user as illustrated by air flow arrows 70. At the same time, expansion of housing 12 to an inhalation state releases the sealed medicament 62 from medicament holder 58 within the air flow chamber 68.

In embodiments using one or more cover portions, this expansion pulls medicament holder cover portion 54, which is mounted on the interior surface 52 of first wall 14, away from opposing second wall 16 or, if two cover portions are included in inhaler apparatus 10, away from medicament holder portion 50 which is mounted on the interior surface 48 of second wall 16. The expansion of housing 12 to the inhalation state breaks the adhesive seal holding medicament holder 58 together and releases the contents thereof within the air flow chamber 68. It will be recognized that the seal between cover portion 54 and either second wall 16 or cover portion 50 must be such that the layers can be peeled apart to expose the drug in the device. Alternatively, though, exposure of the medicament may be provided by using tearable cover portion materials. In such an instance, the shear force exerted on the cover portion(s) as it (they) are pulled by the housing walls during the transition to the inhalation state ruptures at least one of the cover portions to expose the contents thereof, as described below.

In the alternative embodiment where drug is maintained loosely in the interior volume of inhaler apparatus 10 and the ports are covered by port seals, the seals are first removed, inhaler apparatus 10 is expanded as described above and the patient delivers the medicament content of inhaler apparatus 10 by placing the air outlet port or mouthpiece 20 against his or her lips and inhaling.

Referring now particularly to FIGS. 7 and 8, cross-sectional views present the operation of the invention in more detail. Particularly, the operation of valve or filter flap 56 is depicted. In FIG. 7, flap 56 comprises a non-porous material, such as foil or plastic film, and is attached to first wall 14 on the opposite side of air inlet port 18 from primary fold 40. Thus, filter flap 56 includes an attached end 72 and a free end 74. At rest, free end 74 rests against first wall 14 and prevents entry of undesirable contaminants into the interior of inhaler apparatus 10. During use, however, free end 74 of filter flap 56 proceeds toward air outlet port 20 as air flow proceeds along arrows 70 through air flow chamber 68. As free end 74 moves in this manner, filter flap 56 extends substantially vertically into the interior of inhaler apparatus 10, which prevents some portion of medicament 62 from spilling from inhaler apparatus 10 via air inlet ports 18 or from being blown from the device should the user erroneously exhale through the device. This feature facilitates the consumption of the predetermined unit dose of medicament 62 provided in inhaler apparatus 10.

In FIG. 8, an alternative configuration is shown wherein filter flap 56 comprises a porous filter material. Thus filter flap 56 is attached to first wall 14, around its periphery, including its ends 72, 74. The pores of filter flap 56 are of a sufficiently small diameter to preclude entry into the interior of apparatus 10 of unwanted particulate contaminants, while at the same time allowing for air to flow through apparatus 10 along the path described by arrows 70. Additionally, the pores of filter flap 56 may be of a sufficiently small diameter to preclude the loss of medicament 62 through air inlet port 18. Thus, the provision of filter flap 56 facilitates the administration of an appropriate unit dose to the patient using inhaler apparatus 10 in that substantially all of medicament 62 passes out of inhaler apparatus 10 through air outlet port 20 along the air path described by arrows 70 and into the patient's lungs.

As described with reference to FIGS. 7 and 8, filter flap 56 may serve several functions. Flap 56 can permit the passage of air through air inlet ports 18 so that medicament within inhaler apparatus 10 can be inhaled. When a porous material is used, flap 56 prevents the entry of undesirable particles into the interior of housing 12. When a non-porous material is used, flap 56 prevents a person using inhaler apparatus 10 from exhaling through the air outlet and blowing the dose out of the air flow chamber through the air inlet ports prior to inhaling the dose into his or her lungs. It will be appreciated by those of ordinary skill, that a variety of other mechanisms for preventing medicament from being blown through air inlet port 18 may also be used, such as a one-way valve, a duck bill valve, etc. Likewise, such a mechanism may be positioned at various points within housing 12. In the preferred embodiment described above it is positioned at air inlet port 18. However, a valve mechanism could also be positioned in a more proximal position, such as between the medicament 62 and air outlet port or mouthpiece 20.

As will be appreciated by those of skill in the art, and as shown in FIGS. 3, 5, 6, 7 and 8, inhaler apparatus 10 can optionally include additional features to suitably deagglomerate the micronized or particulate drug when the inhaler is used in the manner described above. For instance, the deagglomerating mechanisms include any known to those of ordinary skill, and include, without limitation the following: inhaler apparatus 10 may be fitted with deagglomerator D, shown in one embodiment as a mesh screen, which is positioned between medicament 62 and mouthpiece 20 upon which medicament 62 impacts upon inhalation to break up agglomerated drug particles and increasing fine particle mass. Alternatively, inhaler apparatus 10 may include angled abutment surfaces for creating a tortuous walled pathway through which medicament 62 passes and impacts against during inhalation to achieve the same results. Further still, the selected cover portion 50 or 54 or which the drug is positioned, may be made of a suitable material and affixed to the selected interior surface of housing 12 in such a manner that the selected cover portion vibrates upon inhalation, again assisting in deagglomeration.

ADDITIONAL EMBODIMENTS

Figure 9A:
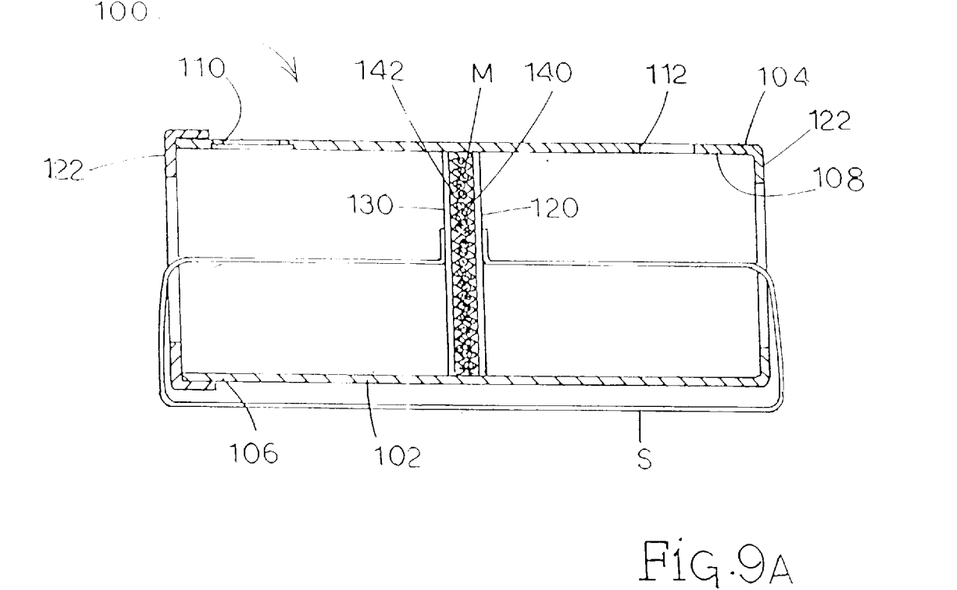
FIGS. 9A and 9B of the drawings are cross-sectional views of an alternative embodiment of an inhaler apparatus of the present invention.
Figure 9B:
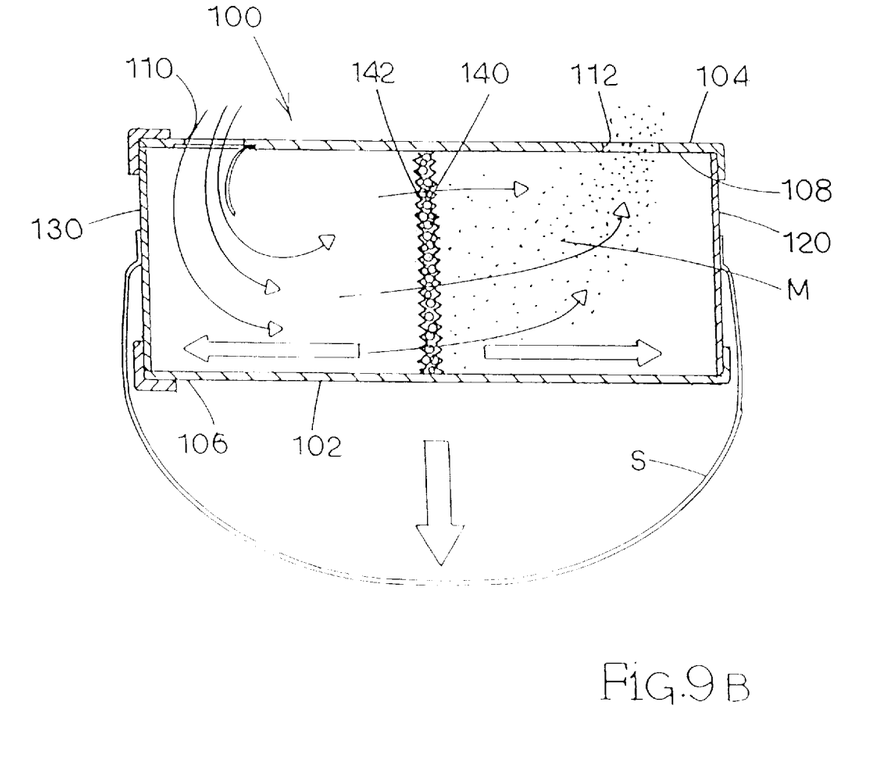

It is envisioned according to this invention that the inhaler apparatus described above can also be presented in different housing configurations. For instance and as shown in FIGS. 9A and 9B, inhaler apparatus 100 has a housing 102, which can be tubular, having a proximal end 104, a distal end 106 and a central bore 108 extending therebetween. In such an embodiment, an air inlet 110 is defined in housing 102 within the region of distal end 106 and air outlet 112 is defined within the region of proximal end 104. A first wall 120 and a second wall 130 are positioned within central bore 108 and are movable along the internal length of central bore 108. Medicament M can be maintained on or packed in beads between deagglomeration screens 140 and 142. In the non-inhalation state, walls 120 and 130 are located between the air ports 110 and 112. A seal can be present between the inner length of housing 102 and peripheral edges of walls 120 and 130 to prevent medicament M from movement. In this non-inhalation state, the internal volume of housing 102 between walls 120 and 130 is minimal and no air flow chamber is yet formed between air inlet 110 and air outlet 112.

To prepare such an embodiment for use, walls 120 and 130 are drawn to their inhalation state by pulling them away from each other and toward opposite ends of housing 102 as shown in FIG. 9B. String S can be used to accomplish such movement of walls 120 and 130 by a user pulling the strings. By this movement, the internal housing volume is increased and, as walls 120 and 130 are drawn past air outlet 112 and air inlet 110, respectively, an air flow chamber is formed within central bore 108 between air inlet 110 and air outlet 112. Suitable means, such as inwardly directed lips 122 may be suitably placed at central bore 108 to prevent walls 120 and 130 from being withdrawn from the bore completely.

For use in the inhalation state, the user inhales through air outlet 112 to cause an air flow within central bore 108. Particles of medicament M are entrained in the air flow and the drug can be carried to the lungs of the user.

Figure 10:
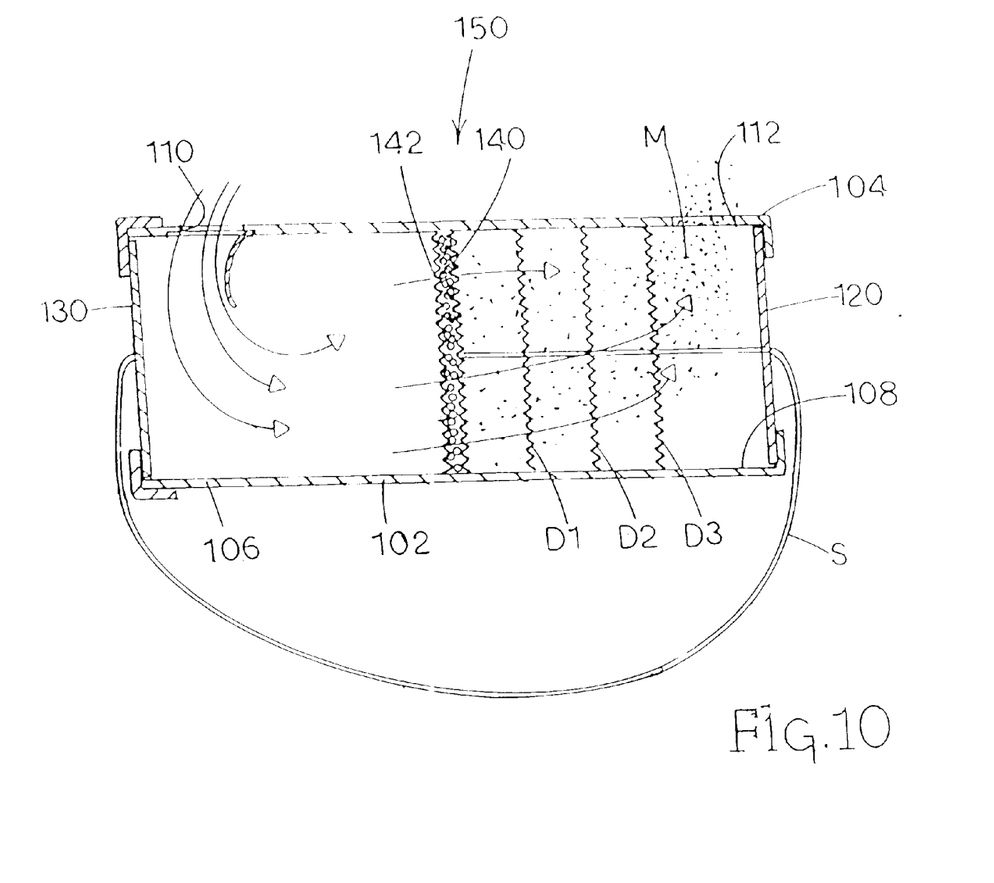
FIG. 10 of the drawings is a cross-sectional view of an inhaler apparatus of FIGS. 9A and 9B with a series of deagglomerators.

An additional embodiment of an inhaler apparatus according to the present invention is shown in FIG. 10 wherein inhaler apparatus 150 is illustrated and is very similar to inhaler apparatus 100 of FIGS. 9A and 9B. Inhaler apparatus 150, however, differs by including a series of additional, spaced-apart deagglomerators D1, D2 and D3, which are illustrated in a preferred embodiment as screens. Deagglomerators D1, D2 and D3 are attached to string S which, in this embodiment, extends through one end of housing 102 and to deagglomerator screen 140. Upon moving the device from the non-inhalation state to the inhalation state, deagglomerators D1, D2 and D3 are moved from a stacked arrangement against screen 140 and the positions depicted in FIG. 10, to aide in further breaking up agglomerated powder particles.

Figure 11A:
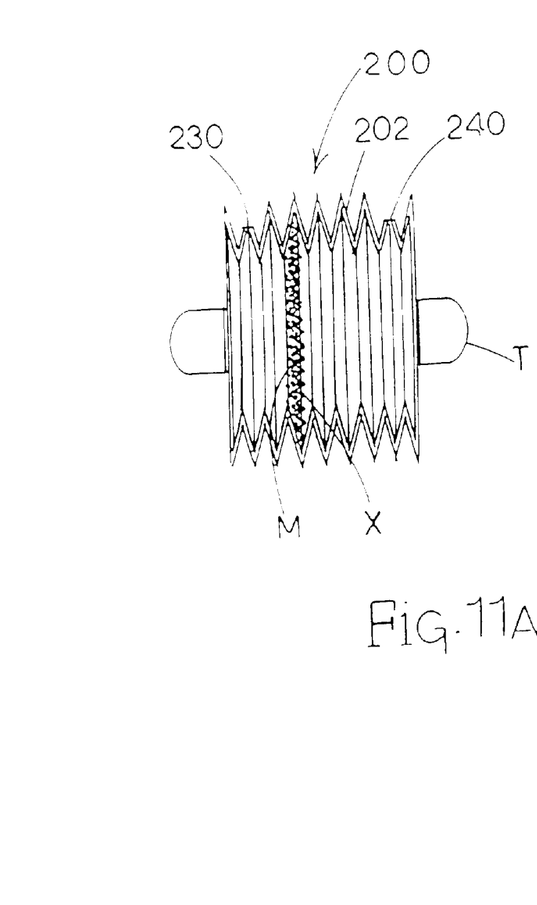
FIGS. 11A and 11B of the drawings are cross-sectional views of another alternative embodiment of an inhaler apparatus of the present invention.
Figure 11B:
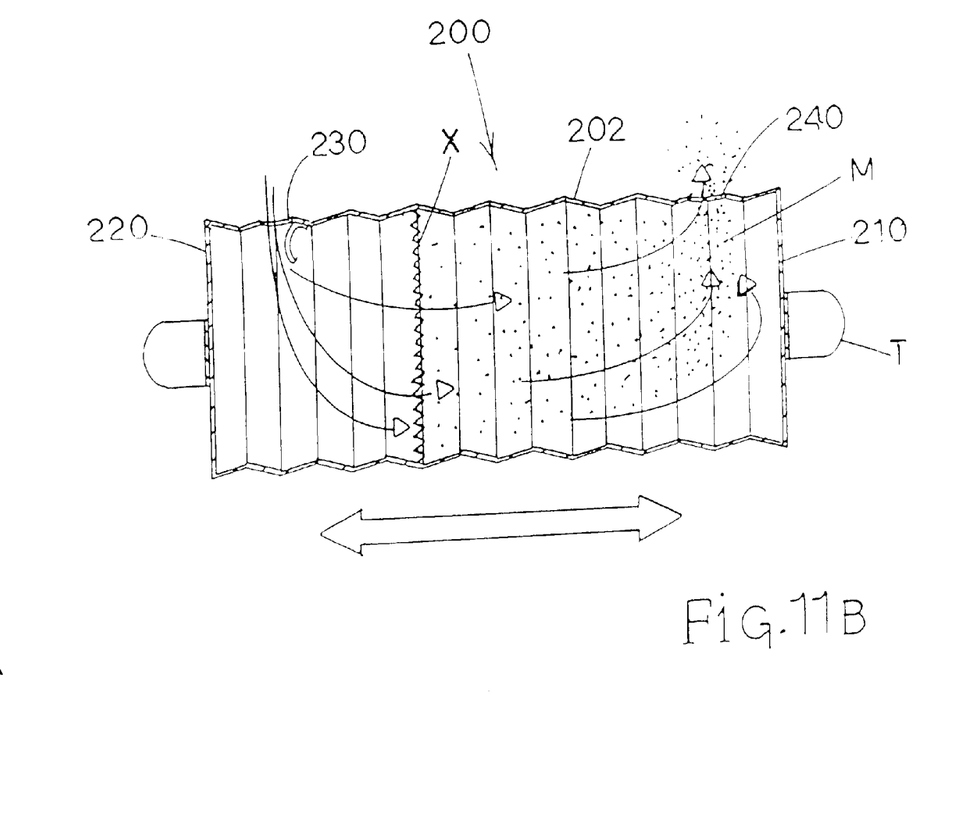

In still another alternative embodiment and as shown in FIGS. 11A and 11B, inhalation apparatus 200 comprises a housing 202 having an expandable and collapsible accordion-like length. A first wall 210 is at one end of the housing, and a second wall 220 is at the opposite end. An air inlet port 230 and an air outlet port 240 are formed in opposite ends of housing 202, in walls 210 and 220 or in the length of the housing. A medicament dose M is positioned medially in the length of the housing between the ends, as medicament M is attached to a substrate X which in FIGS. 11A and 11B takes the form of a mesh.

In the non-inhalation state, this accodian embodiment is collapsed, compressed into a compact, low profile package. In this non-inhalation state, the internal volume is minimal, as walls 210 and 220 are in close proximity to each other, and medicament M is positioned therebetween. Air inlet port 230 and air outlet port 240 are suitably covered to prevent an air flow chamber from being formed therebetween.

To prepare this accordian embodiment of FIG. 11A for use in its inhalation state, air inlet and outlet ports 230 and 240 are unsealed, and walls 210 and 220 are drawn away from each other by pulling tabs T thus expanding housing 202. Upon expansion, as seen in FIG. 11B, the internal housing volume is increased and an airflow chamber is created within housing 202. The user then may inhale through air outlet port 240, entrain medicament M in the inhalation stream and deliver medicament M to his or her lungs.

As will be appreciated by those of ordinary skill, medicament M may be suitably packaged in these additional embodiments in the same fashion described for all other embodiments: a medicament holder may be formed between the first and second walls themselves, may comprise a single cover portion layer and one wall, or may comprise two cover portions sealed to form an envelope.

The medicament may also be carried by substrates. Examples of substrates include mesh substrates loaded with drug and fixed within the housing between the walls; or beads loaded with drug and positioned between containment screens within the device.

Unidirectional flow valves and deagglomerators can also be incorporated within such alternative devices as described above. Deagglomerators can be fitted into the alternative housings which would act to break up larger particulate agglomerates. For instance, one or more screens may be placed within the bore of the tubular embodiment or the baffles embodiment, also between the movable walls. The screens may be linked to each other at slight distances by one or more strings or leaders to form a tow line, such as that depicted in FIG. 10. One end of the tow line is anchored at a location within the housing, and the other to the wall toward the proximal end of the device. When the proximal-most wall is drawn toward its inhalation state, the screen(s) also move proximally. The leader(s) making up the tow line distances the screens at intervals along the air chamber path as the device is configured to its inhalation state. In use, the user inhales into the outlet port, draws the medicament into the air flow stream, where the medicament impacts the successive deagglomeration screens, assisting any particle agglomerates to break up prior to exiting the air outlet port.

Based on the foregoing detailed description, it is apparent to one having ordinary skill in the art that an inhaler apparatus of this invention is small and compact and is therefore easily carried upon the person of a user. Given the preferred construction of paper and foil, an inhaler apparatus of this invention is also inexpensive to manufacture and can be discarded after its unit dose is consumed. An inhaler apparatus of this invention is also easy to use, thus addressing the problem of patient compliance with prescribed instructions associated with delivery of the medicament. Patient compliance is also facilitated in that inhaler apparatus 10 is easily carried on the patient's person.

It is also seen that a method for preparing medicament for inhalation as well as a method for delivering medicament by inhalation are provided.

It will be understood that various details of the invention may be changed without departing from the scope of the invention. Furthermore, the foregoing description is for the purpose of illustration only, and not for the purpose of limitation, as the invention is defined by the claims set forth below.

This application of which this description and claims form part, may be used as a basis for priority in respect of any subsequent application. The claims of such subsequent application may be directed to any feature or combination of features described herein. They may take the form of product, composition, process or use claims and may include, by way of example and without limitation, one or more of the following claims.

What is claimed is:

1. An inhaler apparatus comprising:
    (a) a housing having first and second walls and defining an air inlet and air outlet, said housing having an internal housing volume, said first and second walls being at least partially movable relative to each other so as to expand said internal housing volume from a non-inhalation state, wherein said internal housing volume has a first volume, to an inhalation state, wherein said internal housing volume has a second volume, said second volume being larger than said first volume, and said housing defining an air flow chamber between said air inlet and said air outlet when said housing is in said inhalation state; and
    (b) a medicament holder containing a dose of dry powder medicament positioned between said first and second walls between said air inlet and said air outlet when said housing is in said non-inhalation state, said medicament being exposed within said air flow chamber when said housing is in said inhalation state,
    (c) medicament contained between said first and second walls, said medicament being exposed within said air flow chamber when said housing is in said inhalation state.

2. The inhaler apparatus of claim 1, wherein said medicament holder comprises said first and second walls.

3. The inhaler apparatus of claim 1, wherein said medicament holder comprises at least one cover portion attached to at least said first wall of said housing.

4. The inhaler apparatus of claim 3, wherein said cover portion is constructed of foil.

5. The inhaler apparatus of claim 1, wherein said medicament holder comprises two, opposing cover portions and wherein one of said two cover portions is attached to said first wall of said housing and the other of said two cover portions is attached to said second wall of said housing.

6. The inhaler apparatus of claim 1, wherein said housing is substantially planar in said non-inhalation state and substantially non-planar in said inhalation state.

7. The inhaler apparatus of claim 1, wherein said housing is constructed of paper.

8. The inhaler apparatus of claim 1, wherein said medicament comprises one or more therapeutic or diagnostic agents or combination thereof.

9. The inhaler apparatus of claim 8, wherein said dose of medicament is contained within a single medicament holder.

10. The inhaler apparatus of claim 8, wherein said dose of medicament comprises two separate agents each contained within separate medicament holders.

11. The inhaler apparatus of claim 1, wherein said medicament is selected from the group consisting of analgesic, anginal preparation, antiallergic, anti-infective, antihistamine, anti-inflammatory, antitussive, bronchodilator, corticosteroid, diuretic, anticholinergic, hormone, xanthine, therapeutic protein or peptide, vaccine, diagnostic agent or gene therapy agent.

12. The inhaler apparatus of claim 11, wherein medicament is selected from the group consisting of codeine, dihydromorphine, ergotamine, fentanyl, morphine, diltiazem, cromoglycate, ketotifen, nedocromil, cephalosporins, penicillins, streptomycin, sulphonamides, tetracyclines, pentamidine, methapyrilene, beclomethasone dipropionate, fluticasone propionate, flunisolide, budesonide, rofleponide, mometsasone furoate, triamcinolone acetonide, noscapine, albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, (—)-4-amino-3,5-dichloro--[[[6-[2-(2-pyridinyl)ethoxy]-hexyl]methyl] benzenemethanol, amiloride, ipratropium, tiotroprium, atropine or oxitropium, cortisone, hydrocortisone or prednisolone, aminophylloine, choline theophyllinate, lysine theophyllinate or theophylline, insulin or glucagon, or salts, esters, or solvates thereof, alone or in combination.

13. The inhaler apparatus of claim 1, wherein said dose of medicament is releasably retained on a substrate.

14. The inhaler apparatus of claim 13, wherein said substrate is selected from the group consisting of spheres, meshes, fibers or films.

15. The inhaler apparatus of claim 1, further comprising a valve carried by said housing, said valve allowing unidirectional air flow through said housing.

16. The inhaler apparatus of claim 15, wherein said valve allows unidirectional air flow from said air inlet to said air outlet.

17. The inhaler apparatus of claim 1, further comprising a deagglomerator within said housing between said air inlet and air outlet.

18. The inhaler apparatus of claim 17, wherein said deagglomerator is positioned between said medicament and said air outlet when said housing is in said inhalation state.

19. The inhaler apparatus of claim 1, wherein said housing is tubular with said first and second walls movably positioned within said tubular housing such that in said inhalation state, said first and second walls are spaced-apart from one another with each of said first and second walls positioned substantially at opposite ends of said tubular housing.

20. The inhaler apparatus of claim 19, wherein said tubular housing is collapsible between the opposite ends of said tubular housing.

21. The inhaler apparatus of claim 1, wherein said housing and said first and second walls are integral.

22. An inhaler apparatus comprising of:
  (a) a flexible housing having first and second walls, said housing defining an air inlet and an air outlet and an internal housing volume, said housing being compressible from a non-inhalation state wherein said housing is substantially planar to an inhalation state wherein said housing is substantially non-planar to expand said housing volume wherein an air flow chamber is defined within said housing between said air inlet and said air outlet in said inhalation state of said housing; and
  (b) a medicament holder for containing medicament in a sealed manner when said medicament holder is in a closed position, said medicament holder having an internal holder volume and said medicament holder being positioned within said housing between said first and second walls, said medicament holder further comprising first and second cover portions attached, respectively, to inner sides of first and second walls of said housing such that compression of said housing to expand said housing volume pulls apart said first and second cover portions to open said medicament holder from its closed position;
  whereby said medicament holder is closed when said housing is in said substantially planar, non-inhalation state and said medicament holder is open with its holder volume exposed to said air flow chamber when said housing is in said substantially non-planar, inhalation state.

23. A method for delivering medicament for inhalation, said method comprising the steps of:
  (a) providing an inhaler apparatus comprising:
    (I) a housing having first and second walls and defining an air inlet and an air outlet, said housing and said first and second walls defining an internal housing volume, said first and second walls being at least partially movable relative to each other so as to expand said internal housing volume from a non-inhalation state, wherein said internal housing volume has a first volume, to an inhalation state, wherein said internal hosing volume has a second volume, said second volume being larger than said first volume, and said housing defining an air flow chamber between said air inlet and said air outlet when said housing is in said inhalation state; and
    (ii) a medicament holder containing a dose of dry powder medicament positioned between said first and second walls between said air inlet and said air outlet when said housing is in said non-inhalation state; and
  (b) moving said first and second walls to said inhalation state to breach said medicament holder and thereby expose said medicament to said air flow chamber; and
  (c) creating an air flow through said air flow chamber from said air inlet to said air outlet to deliver said medicament from said inhaler apparatus through said outlet.

24. The method of claim 23, wherein said first and second walls of said housing of said inhaler are moved to expose said medicament to said air flow chamber by compressing said housing to expand said housing volume.

25. The method of claim 23, wherein a user inhales from said air outlet of said inhaler apparatus to create said air flow through said air flow chamber and further comprising the step of said user subsequently inhaling said medicament.

26. The method of claim 23, further comprising the step of deagglomerating said medicament by use of a deagglomerator within said housing.

27. A method of preparing medicament for inhalation within an inhaler apparatus, said method comprising the steps of:
  (a) providing an inhaler apparatus comprising a housing having an air inlet and an air outlet and an internal housing volume, and a medicament holder containing a dose of dry powder medicament, said holder being positioned between said air inlet and said air outlet, said holder acting as a barrier between said dose and said air inlet and said air outlet; and (b) expanding said internal housing volume of said inhaler apparatus to form an air flow within said inhaler apparatus and simultaneously breaching said medicament holder thereby exposing previously unexposed medicament within said housing volume of said inhaler apparatus to said air flow chamber whereby said medicament is prepared for inhalation and wherein said step of paragraph (a) causes and occurs substantially simultaneously with exposure of said medicament to said air flow chamber.

28. A method of delivering a medicament to a user by inhalation, said method comprising the steps of preparing medicament for inhalation according to the steps of claim 27 and further comprising a last step of a user inhaling said medicament through an air outlet of said inhaler apparatus.

29. An inhaler apparatus comprising:
   (a) a flexible housing having first and second walls, said housing defining an air inlet and an air outlet and an internal housing volume, said housing being deformable so as to expand said housing volume from a non-inhalation state wherein said housing is substantially planar to an inhalation state wherein said housing is substantially non-planar and wherein an air flow chamber is defined within said housing between said air inlet and said air outlet; and
   (b) a medicament holder for containing medicament in a sealed manner when said medicament holder is in a closed position, said medicament holder having an internal holder volume and said medicament holder being positioned within said housing between said first and second walls, said medicament holder further having at least one cover portion attached to at least said first wall of said housing such that said cover portion is pulled by expansion of said housing volume to said inhalation state to open said medicament holder from its closed position;
whereby said medicament holder is closed when said housing volume is in said substantially planar, non-inhalation state and said medicament holder is open with its internal holder volume exposed to said air flow chamber when said housing volume is in said substantially non-planar, inhalation state.

30. The inhaler apparatus of claim 29, wherein said medicament holder comprises two, opposing cover portions and wherein one of said two cover portions is attached to said first wall of said housing and the other of said two cover portions is attached to said second wall of said housing.

31. The inhaler apparatus of claim 29, wherein said housing is constructed of paper and said cover portion is constructed of foil.

32. A method for delivering medicament for inhalation, said method comprising the steps of:
   (a) providing an inhaler apparatus comprising:
      (i) a flexible housing having first and second walls, said housing defining an air inlet and an air outlet and an internal housing volume, said housing being deformable so as to expand said housing volume from a non-inhalation state wherein said housing is substantially planar to an inhalation state wherein said housing is substantially non-planar and wherein an air flow chamber is defined within said housing between said air inlet and said air outlet; and
      (ii) a medicament holder having an internal holder volume containing medicament, said medicament holder positioned within said housing between said first and second walls and said medicament holder having at least one cover portion attached to at least said first wall of said housing;
   (b) deforming said housing to expand said housing volume and thereby open said medicament holder and expose said medicament to said air flow chamber; and
   (c) creating an air flow through said air flow chamber from said air inlet to said air outlet to deliver said medicament from said inhaler apparatus through said air outlet.

33. The method of claim 32, wherein said housing of said inhaler apparatus is deformed by compressing said housing to expand said housing volume.

34. The method of claim 33, wherein a user inhales from said air inlet of said inhaler apparatus to create said air flow through said air flow chamber and further comprising the step of said user subsequently inhaling said medicament.

\* \* \* \* \*

UNITED STATES PATENT AND TRADEMARK OFFICE
CERTIFICATE OF CORRECTION

PATENT NO. : 6,098,619
DATED : August 8, 2000
INVENTOR(S) : I. L. Britto, et. al.

It is certified that error appears in the above-identified patent and that said Letters Patent are hereby corrected as shown below:

On first page at [30] Foreign Application Priority Data where it reads: "[DE] Germany...9810126" change to ---[GB] Great Britian...9810126.4 ---

Claim 1, in beginning of line 20, delete [©] and replace with ---(c)---

Claim 23, in beginning of line 4, delete [I] and replace with ---(i)---

Claim 23, in beginning of line 25, delete [©] and replace with ---(c)---

Signed and Sealed this

Fifteenth Day of May, 2001

Attest:

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT NO. : 6,098,619
DATED : August 8, 2000
INVENTOR(S) : I. L. Britto, et al.

It is certified that error appears in the above-identified patent and that said Letters Patent is hereby corrected as shown below:

Title page at item [30] Foreign Application Priority Data where it reads:
"[DE] Germany...9810126" change to --- [GB] Great Britian...9810126.4 ---

Claim 1, in beginning of line 20, delete [©] and replace with --- (c) --
Claim 23, in beginning of line 4, delete [I] and replace with ---(I) ---
Claim 23, in beginning of line 25, delete [©] and replace with --- (c) ---

Signed and Sealed this

Thirty-first Day of July, 2001

Attest:

*Nicholas P. Godici*

Attesting Officer

NICHOLAS P. GODICI
*Acting Director of the United States Patent and Trademark Office*